(12) United States Patent
Von Duyke et al.

(10) Patent No.: US 6,631,714 B2
(45) Date of Patent: Oct. 14, 2003

(54) TISSUE DILATOR DEVICES, METHODS OF FABRICATION OF TISSUE DILATORS, AND METHODS OF USE FOR TISSUE DILATORS

(75) Inventors: Andrew L. Von Duyke, Minnetonka, MN (US); James B. Easley, Orono, MN (US); David F. Kreitzer, Scottsdale, AZ (US); Dan B. Pool, Scottsdale, AZ (US)

(73) Assignee: CNS, Inc., Eden Prairie, MN (US)

( * ) Notice: Subject to any disclaimer, the term of this patent is extended or adjusted under 35 U.S.C. 154(b) by 0 days.

(21) Appl. No.: 09/896,213

(22) Filed: Jun. 29, 2001

(65) Prior Publication Data

US 2002/0000227 A1 Jan. 3, 2002

Related U.S. Application Data

(60) Provisional application No. 60/214,995, filed on Jun. 29, 2000, provisional application No. 60/215,024, filed on Jun. 29, 2000, and provisional application No. 60/221,108, filed on Jul. 27, 2000.

(51) Int. Cl.[7] .............................................. A61M 16/00
(52) U.S. Cl. .................. 128/200.24; 606/199
(58) Field of Search ....................... 128/200.24, 200.12, 128/207.18, 848; 606/199, 191, 196

(56) References Cited

U.S. PATENT DOCUMENTS

| | | |
|---|---|---|
| 1,292,083 A | 1/1919 | Sawyer |
| 5,391,182 A | 2/1995 | Chin ........................... 606/213 |
| 5,476,091 A | 12/1995 | Johnson .................. 128/200.24 |
| 5,533,499 A | 7/1996 | Johnson .................. 128/200.24 |
| 5,533,503 A | 7/1996 | Doubek et al. ........ 128/200.24 |
| 5,546,929 A | 8/1996 | Muchin ................. 128/200.24 |
| 5,549,103 A | 8/1996 | Johnson .................. 128/200.24 |
| 5,553,605 A | 9/1996 | Muchin ................. 128/200.24 |
| 5,611,333 A | 3/1997 | Johnson .................. 128/200.24 |
| 5,653,224 A | 8/1997 | Johnson .................. 128/200.24 |
| 5,816,241 A | * 10/1998 | Cook ..................... 128/200.24 |
| 6,058,931 A | * 5/2000 | Muchin ................. 128/200.24 |
| 6,352,548 B1 | * 3/2002 | Blach et al. ................ 606/199 |
| 6,375,667 B1 | * 4/2002 | Ruch ........................... 606/199 |
| 6,453,901 B1 | * 9/2002 | Ierulli .................. 128/200.24 |
| 6,470,883 B1 | * 10/2002 | Beaudry ................ 128/200.24 |

FOREIGN PATENT DOCUMENTS

WO            9742918          11/1997

* cited by examiner

*Primary Examiner*—William C. Doerrler
(74) *Attorney, Agent, or Firm*—Fulbright & Jaworski L.L.P.

(57) ABSTRACT

The invention is directed to devices and methods for tissue dilators. The present invention encompasses a large variety of discrete structure, all intended to be applied externally to a subject for the purpose of dilating, or lifting, tissue adjacent to nasal passageways of the subject, including the vestibule and/or the valve of the subject so as to decrease resistance to inhalation and exhalation of said subject during respiration. The dilator comprises an alignment feature which is aligned with the uses nasal ridge during application to ensure a proper application.

13 Claims, 18 Drawing Sheets

TISSUE DILATOR DEVICES, METHODS OF FABRICATION OF TISSUE DILATORS, AND METHODS OF USE FOR TISSUE DILATORS

This application for utility patent coverage in the United States of America hereby incorporates by reference and, under 35 U.S.C. §119(e), claims the benefit of the contents and filing dates accorded three (3) U.S. Provisional patent applications bearing application Ser. Nos. 60/215,024; 60/214,995; and 60/221,108 and filed on Jun. 29, 2000, Jun. 29, 2000 and Jul. 27, 2000, respectively. All three (3) said U.S. Provisional applications are commonly entitled, "Tissue Dilators and Methods."

FIELD OF THE INVENTION

The present invention is directed to tissue dilators. In preferred embodiments, the tissue dilator devices, methods of fabrication of tissue dilators, and the methods of use for tissue dilators are particularly advantageous for use as nasal dilators for supporting nasal tissues or dilating nasal tissues overlying nasal passages such as the valve and/or the vestibule portion of such nasal passages.

BACKGROUND OF THE INVENTION

The present invention is directed to externally applied tissue dilators and methods of fabrication and use of such external tissue dilators to dilate nasal tissue of a subject. Some examples of presently known nasal dilators are disclosed in, for example, U.S. Pat. Nos. 5,476,091; 5,533,503; 5,546,929; 5,549,103; 5,553,605; 5,611,333; and 5,653,224, the entire disclosures of which are incorporated herein by reference.

SUMMARY OF THE INVENTION

The present invention relates to tissue dilator devices, methods of fabrication of tissue dilators, and methods of use for tissue dilators. In particular, the present invention relates to a wide variety of tissue dilators adapted to be coupled to a local tissue region of a nose to dilate interior nasal passages of a subject including the vestibule and/or the valve thereof. The present invention is not intended to be limited to the illustrated or described embodiments as they are intended merely to assist the reader of this disclosure in understanding the subject matter of the invention described, taught, enabled and depicted herein. For example, whether or not a single dilator device is depicted as adhered to a local tissue region of a single nose, more than one device, and different such dilator devices may couple to a single nose to create a desired level of dilation of said nose. Also, in those embodiments depicting a resilient member or region of resiliency to promote dilation more than a single such resilient member or region of resiliency may be utilized within or in conjunction with a single supporting body adhered to a local tissue region. Said resilient member(s) or regions of resiliency may be differing size, area, thickness, length or shape while still remaining within the purview and scope of the present invention. Likewise, use of one or more release layers in conjunction with pressure sensitive or other adhesives preferably used in conjunction with the inventive dilator devices of the present invention may be used to enhance the shelf life, ease of use and shipment, comfort to a user and the like as is presently known and used in the art. Furthermore, the present invention draws upon the long and continually developing art and science of extrusion for certain of the embodiments of the present invention and one of skill in such art and science will readily appreciate the applicability of certain of said embodiments to such manner of fabrication. The inventors hereof assert that an ideal manner of external nasal dilation preferably provides a lifting force orthogonal to the local tissue region, but some of the embodiments of this invention provide a tensing force (or surface tension across the plane of said local tissue region) so that a lower magnitude lifting force produces a desired amount of nasal dilation. Some of the embodiments of the present invention provide for reuse of certain components of the nasal dilators of the present invention so that other components may be reused. In these embodiments, the reuse may be only an additional reuse while others may provide for long term "reuse" of the entire nasal dilator. In some regard, the devices depicted, taught, enabled and disclosed herein are representative of entire families of new, useful and non-obvious tissue dilators having a variety of alternate embodiments. As a result of a single or a few illustrations of one or more such alternative embodiment, the remaining alternate embodiments should not be restricted, but rather are expressly covered hereby.

As for tissue dilator devices, the present invention encompasses a large variety of discrete structure, all intended to be applied externally to a subject for the purpose of dilating, or lifting, tissue adjacent to nasal passageways of the subject, including the vestibule and/or the valve of the subject so as to decrease resistance to inhalation and exhalation of said subject during respiration. The tissue dilators of the present invention include those having at least one resilient member providing a first biasing force, or restoring force, so that when mechanically coupled to dilate adjacent tissue of a subject, the dilator constantly exerts a restoring force developed to return the resilient member to an unbent state. In addition, a second (or additional) biasing force or forces may be applied in combination to assist in producing a desired dilation of tissue of a subject that acts in concert with the first biasing force to impart an additional amount of force to dilate tissue of a subject.

As for methods of fabrication of tissue dilator devices, the present invention teaches and enables those of skill in the manufacturing art to rapidly and efficiently produce the tissue dilator devices described herein. That is, in addition to existing methods and techniques for fabrication of tissue dilators, the present invention adds several new methods and techniques for fabricating tissue dilators according to the present invention.

As for methods of use of such tissue dilators, the present invention teaches and enables several inventive methods of use of tissue dilators for the devices described herein, methods of use and application of such devices to a local tissue region and methods of fabrication as well.

BRIEF DESCRIPTION OF THE DRAWINGS

In the following drawings elements having common attributes are referred to with a common reference numeral even though illustrated embodiments having such common attributes may be patentably distinct from other of said illustrated embodiments.

DETAILED DESCRIPTION OF THE ILLUSTRATED EMBODIMENT

Figure 4:
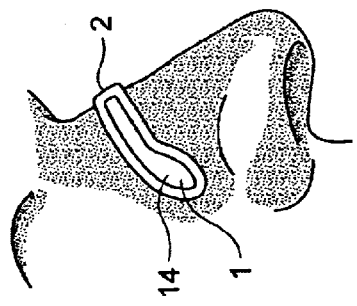

The invention is directed to devices and methods particularly advantageous for use in supporting or dilating nasal tissues overlying a nasal passage to thereby promote ease of respiration in a subject.

The devices and methods of the invention will be described by reference to the accompanying drawings in which oftentimes the same elements are numbered the same throughout. The illustrated embodiments and descriptions are provided only for exemplary purposes to facilitate comprehension of the invention and should not be construed to limit the scope of the invention. The drawings are not described in sequential order, but are often referred to with respect to a common attribute of the embodiments described therein.

In FIGS. 1–38, the disclosed devices can include a base 1 which is applied over a portion or all of the tissue to be supported or dilated. In some embodiments, an over-the-bridge component 2 can also be present. The over-the-bridge component 2 can be integral, separable, or independent of the base 1. The over-the-bridge component 2 may further be integral, separable, or independent of other components or elements herein described. It will be appreciated that in some embodiments, base 1 can be constructed to transfer or exert a force which can compress, tense, displace, support, stretch, shear, lift, etc. a portion or all of the tissue, and surrounding tissue, to which the base is applied.

It is to be understood that the following disclosure describes a number of invention features or aspects through illustrations. Each embodiment illustrated and described under a specific aspect may comprise only that aspect or may comprise other aspects described in another embodiment. For example, one device of the present invention may disclose a multi-component dilator providing adjustable lifting dilation in a multi-directional manner.

Lifting Dilation

One aspect of the present invention relates to devices providing lifting dilation. Lifting dilation forces are forces directed outward (e.g. substantially perpendicular) from the tissue over the nasal passages. A nasal dilator may for example include one lifting dilator comprising a base having a plurality of flaps. An over-the-bridge component can be included, to provide lifting force to opposing skin portions, or local tissue regions, proximate nasal passages, such as the vestibule and valve portions of said nasal passages, to dilate said nasal passages and improve flow of air therethrough. The base may comprise, for example, a triangular frame as illustrated or other base or frame shapes configured for facilitating tissue dilation. This type of arrangement thus provides tissue dilation when, for example, the device is depressed and an adhesive on the flaps attaches to the skin of the nose; upon release, the flaps lift back to their original position thereby dilating the nasal passage.

Lifting dilation can be achieved with or without use of an over-the-bridge component preferably formed of material having a degree of resiliency so that when said component is bent to the contour of a nose, a restoring force is exerted to further promote the lifting dilation. Of course, a lifting force providing dilation may be disposed on either side of a nose or only one side of a nose, or may couple to more than one local tissue region on either side of a nose.

Figure 10:
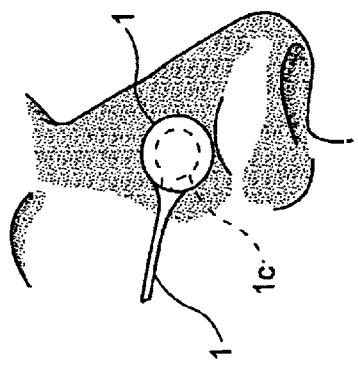

Referring now to FIG. 10, another lifting dilation embodiment of the present invention having a base 1 and a portion 7 which extends away from the lateral aspect of the nose. The base 1 can include a perimeter adhesive surrounding a pad 1c. As shown, for example, the base 1 is placed on either side of the nose. Each portion 7 can then be secured in a position not directly over the bridge of the nose to provide a dilation force. For example, the extending portion 7 can be positioned similar to how a medical mask with thin elastic headbands is worn.

Figure 8:
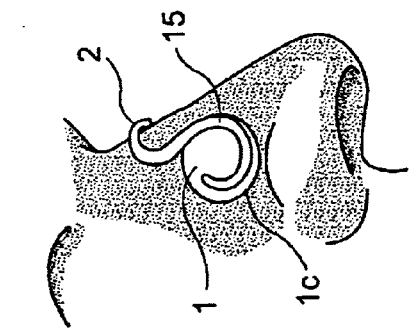

Lifting dilation may also be achieved with devices, as illustrated in FIG. 8, comprising a base 1 and an over-the-bridge component 2. The base 1 may include a pad 1c. The over-the-bridge component 2 may comprise a plastic dilating member 15. The plastic dilating member 15 in this arrangement provides lifting dilation force by tending to return to a planar state after being forced from the planar state by bending.

Multi-Directional Dilation

Figure 1:
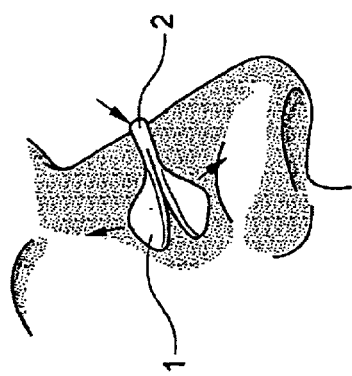
FIG. 1 is one embodiment of a nasal tissue dilator devices positioned on a nose according to the invention; and, FIGS. 2 through 48 are alternative embodiments of a variety of nasal tissue dilator devices positioned on a nose according to the invention.

Another aspect of the present invention includes devices providing multi-directional dilation. Some dilators create lifting forces created from, for example, a spring member over the bridge of the nose tending to return to a planar state. As used herein, a "multi-directional" dilator also provides tensing forces. Tensing forces are forces that stretch or extend the tissue overlying the nasal passage. FIG. 1 illustrates one example of a multi-directional device comprising a base 1 and an over-the-bridge component 2. The base 1 in this embodiment is bifurcated in a manner to exert a tensing force that runs substantially parallel to the bridge of the nose (arrows) in addition to lifting forces directed outward from the nasal passage. In other embodiments, the over-the-bridge component 2 may or may not provide an outwardly directed lifting force.

Without being limited to a particular theory, it is believed that tensing forces stretch the skin taut providing more dilation from the same amount of force needed when the skin is not stretched taut. The tensing forces can be located, for example, parallel to the bridge of the nose as illustrated in FIG. 1. It will be appreciated, however that tensing forces need not only be in the direction indicated by the arrows of FIG. 1, but also in other directions which stretch or extend tissue along the plane in which the base 1 lies. Tensing forces may be applied along the tissue in any direction to increase a device's dilation properties.

Figure 6:
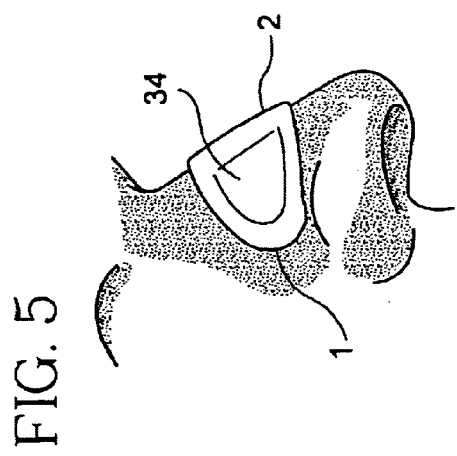

FIG. 6 also discloses a multi-directional dilator comprising a base 1, an over-the-bridge component 2, and a wire-dilating member 3. In this embodiment, the wire-dilating member provides tension forces running substantially parallel to the bridge of the nose ("out" arrows) in addition to outwardly directed forces ("up" arrow). In other embodiments, the wire-dilating member 3 may or may not provide outwardly directed lifting forces.

Adjustable Dilation

Figure 2:
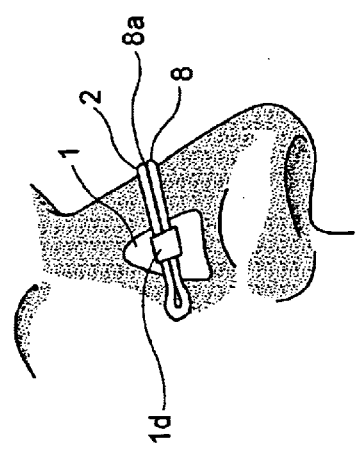

Another aspect of the present invention includes devices providing adjustable dilation. FIG. 2 shows one such embodiment having a base 1 and an over-the-bridge component 2. In this embodiment, the over-the-bridge component 2 comprises an elastic member 8, such as elastic bands 8a. The elastic member 8 crosses over the bridge of the nose and attaches to the base 1. Dilation force can be adjusted while the dilator is being applied. For example, pulling on the elastic member 8 to a selected position and then depressing an adhesive region 1d on the base 1 against the elastic member 8 secures the stretched elastic member 8 to the base 1. Selectively stretching and securing the elastic member adjusts the device's dilation level.

Variable Dilation

Figure 3:
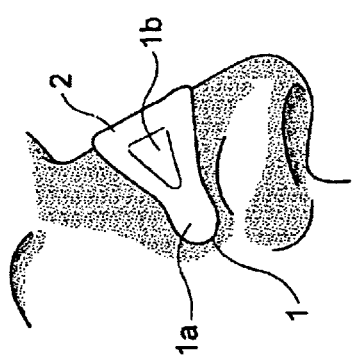

Another aspect of the present invention includes devices providing variable dilation. Variable dilation relates to dilators comprising multiple regions or components with more than one strength of dilation force. FIG. 3 discloses one embodiment providing variable dilation. The illustration shows a device having a base 1 and an over-the-bridge component 2. The base comprises a foundational or first region 1a and a second region 1b. The first region 1a may or may not provide dilation forces over the bridge of the nose. The second region 1b can provide a stronger dilation force than the first region 1a. The dilation force of region 1b in this embodiment extends outwardly from the nasal passages by upward lifting of region 1b around an axis parallel to the bridge of the nose as indicated by hash marks.

Bi-Axial Dilation

Another aspect of the present invention includes devices providing bi-axial dilation. That is, the axis of dilation can be selectively positioned on the nose to a particular orientation to provide a particular direction of lift. FIG. 3 also provides another example of a bi-axial dilator. The axes are shown with hash marks. As illustrated, embodiments can comprise a base 1 having a flap 1b. The flap 1b provides the lift force for dilation on either side of the nose without the use of an over-the-bridge component.

Figure 5:
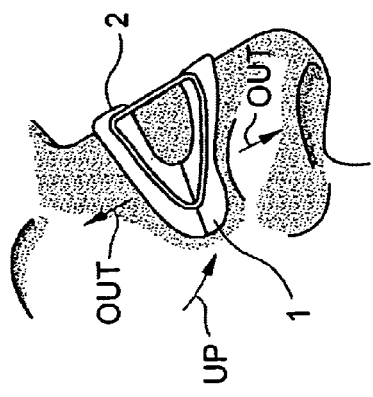

Bi-axial dilation may also be achieved with devices, as illustrated in FIG. 5, comprising a base 1 having a flap 34 and an over-the-bridge component 2. The base 1 may be dilating or non-dilating. The flap 34 can provide dilating force on either side of the nose along an axis running parallel to the bridge of the nose as illustrated with hash marks. For example, the flap 34 pulls the skin tissue outwardly from the nasal passages along an axis parallel to the bridge of the nose to lift the tissue and dilate the nasal passage.

Figure 14:
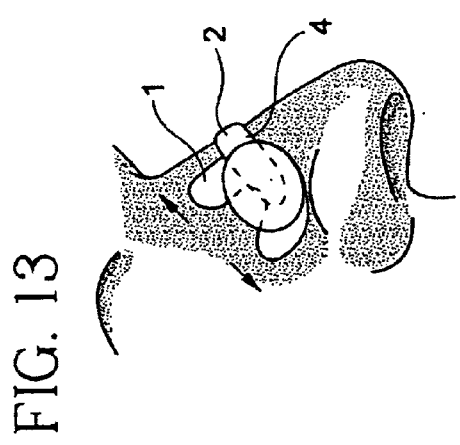
Figure 15:
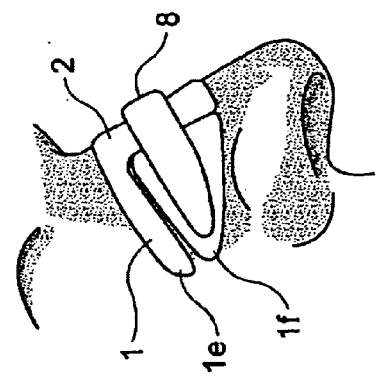
Figure 16:
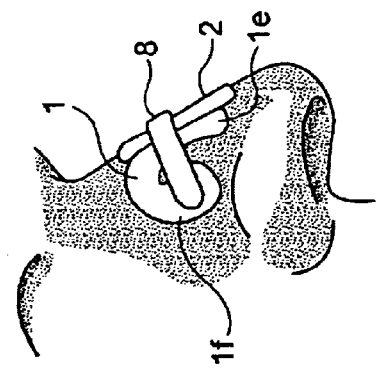

FIGS. 14–16 show other bi-axial embodiments. FIG. 14 illustrates a device comprising a base 1 and an over-the-bridge component 2. The base 1 further comprises a first base portion 1e and a second base portion 1f. Dilation forces in this embodiment are created by the second base portion 1f as opposed to dilation forces from the over-the-bridge component 2. The second base portion 1f is under tension providing dilation forces around parallel axes (hash marked area) on either side of the nose.

FIG. 15 illustrates another bi-axial device comprising a base 1 having a first and second base portion 1e and 1f, an over-the-nose component 2, and an elastic member 8. The elastic member 8 provides dilation by pulling or lifting the second base portion 1f outwardly. The region similar to that region under tension as shown in FIG. 14 may or may not provide tension in this arrangement. FIG. 16 illustrates an arrangement similar to FIG. 15 having components of different shape.

Figure 11:
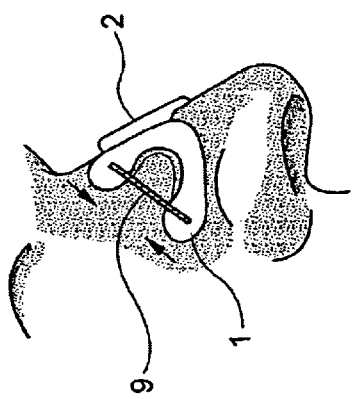

Another bi-axial dilator, as disclosed in FIG. 11, comprises a base 1, an over-the-bridge component 2, and an adjustment element 9. Adjustment element 9 adjusts or creates a force applied to, or near, a portion or all of the tissue to which the base 1 is applied. The adjustment element 9 can, for example, attach to various locations on the base 1 to provide for localized dilation. In this embodiment, the adjustment element 9 pops up or pinches the tissue over the nasal passages in the direction shown by arrows. The pinching causes the nasal passage to lift thereby providing dilation. The over-the-bridge component 2 of this device may be dilating to provide multi-directional dilation or may be non-dilating.

Multi-Component Dilation

Figure 9:
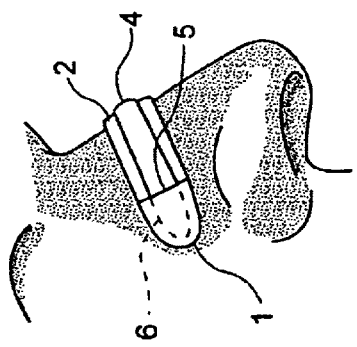

Another aspect of the claimed invention includes devices having multi-components. Multi-component dilators essentially comprise a base, an over-the-bridge component, and a resilient member. The resilient member may or may not be removable. FIG. 9 is an illustration of a multi-component dilator comprising a base 1, an over-the-bridge component 2, and a removable resilient member 4. The base 1 includes a coupler 6 for receiving an end 5 of resilient member 4. Another similar embodiment is set forth at FIG. 23.

The coupler 6 for receiving an end 5 of the resilient member 4 can be selected from, for example, a pocket, pouch, strap, tie, hook and loop, etc. The resilient member 4 may be selected from, for example, plastic, wire, elastic pieces, springs of various materials including shape memory materials, splines, or any other components that produce the desired dilating forces.

In a multi-component embodiment having a removable resilient member, the removable resilient member can be coupled with the base before or after application of the device to the nose. To illustrate use, an adhesive, pocketed, non-dilating base can be applied to the nose and a removable resilient member then placed within pockets of the base on either side of the nose. Once placed into the pockets and forced over the nose from a planar state, the resilient member tends to return to a planar state thereby producing dilating lift forces.

Figure 7:
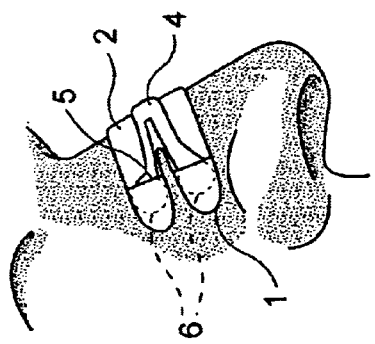
Figure 17:
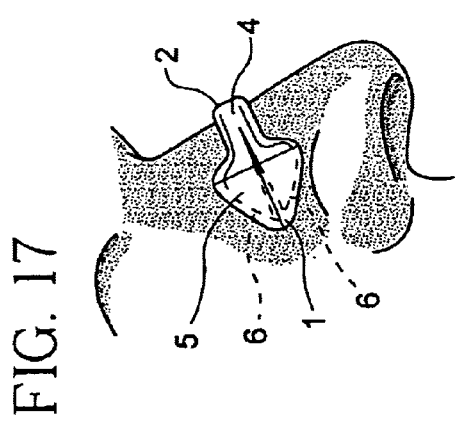

In another embodiment, the resilient member, such as a multi-directional resilient member, can be used to produce tension forces that run, for example, parallel to the bridge of the nose in addition to lifting forces. To illustrate, FIGS. 7 and 17 show some devices comprising a base I having a plurality of couplers 6 for receiving a removable resilient member 4 having a plurality of ends 5. This multi-directional arrangement increases the effectiveness of the dilator by providing both outwardly lifting forces as the resilient member tends to return to a planar state and tension forces to stretch the tissue in a direction parallel to the bridge of the nose.

Figure 13:
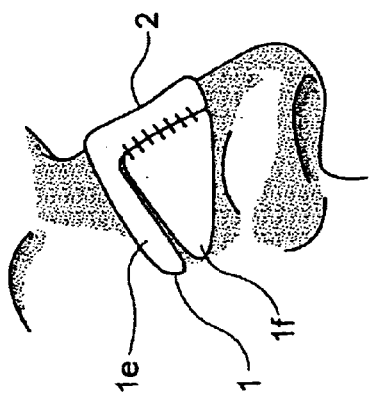

The tension forces of multi-component devices may or may not be directed along an axis running parallel with the bridge of the nose. For example, FIG. 13 illustrates a multi-component dilator including a dilating base 1 and an over-the-bridge component 2 comprising a resilient member 4. This arrangement provides a tension force or stretching of the skin in a direction perpendicular to the bridge of the nose (arrows) as opposed to tension forces running parallel to the bridge of the nose.

Figure 12:
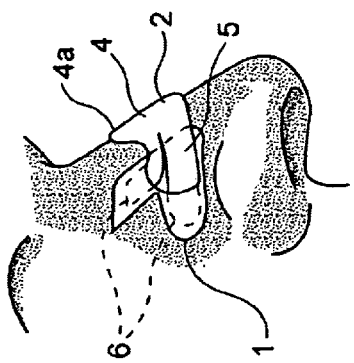

Other multi-component embodiments are shown in FIGS. 12, 18, 19, 22, 25–28, 32–37, each comprising various features. FIG. 12, for example, illustrates a device having a bi-directional resilient member 4 that provides a centering structure 4a. The centering structure 4a facilitates centering of the resilient member 4 on the bridge of the nose. A centering structure 4a can be an integral or separable arrangement of, for example, an over-the-bridge component 2, a resilient member 4, a base 1, or any other component of the present invention. The centering structure 4a can further include, for example, a hump, arch, groove, indicator, taper, notch, etc.

Figure 18:
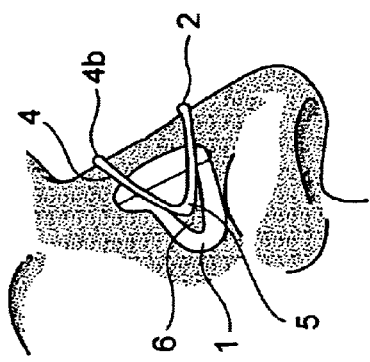
Figure 19:
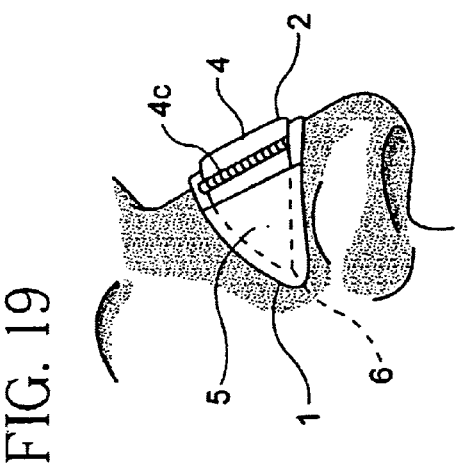

Referring to FIG. 18, embodiments of the multi-component dilator can include various shaped bases 1, various shaped couplers 6, and, for example, a removable resilient member 4 comprising a wire piece 4b. FIG. 19 illustrates a multi-component embodiment comprising a removable resilient member 4 having a grasping member 4c. The grasping member 4c can be selected from, for example, a rim, ridge, wedge, protrusion, notch, cutout, groove, or any other structure or device which allows a user to more easily grasp or handle a resilient member 4.

Figure 22:
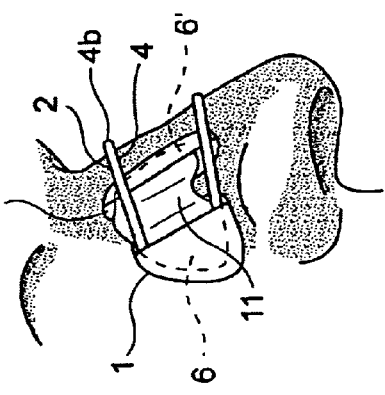
Figure 23:
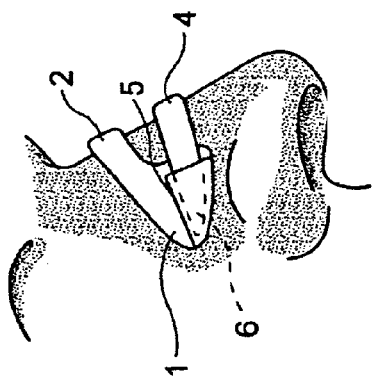

FIG. 22 discloses a multi-component device having a base I and an over-the-bridge component 2, and a resilient member 4 such as a wire piece 4b. Base 1 includes a coupler 6. This device also includes an additional base 1' having a coupler 6' and a second dilating element 11. The wire piece 4b connects with coupler 6 while the second dilating element 11 connects with both couplers 6 and 6'. The wire piece 4b provides outwardly lifting dilation forces while the second dilating element 11 provides tension forces. This arrangement increases the effectiveness of the device's dilating properties by providing multi-directional dilating forces.

Figure 25:
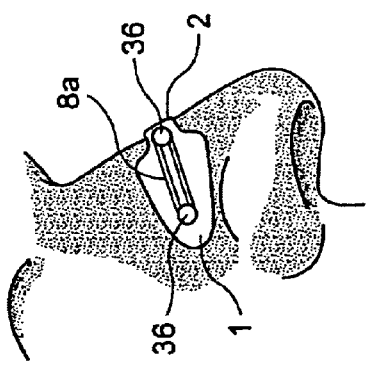

In yet another embodiment, as shown in FIG. 25, a multi-component dilator can comprise a base 1 having one or more securing elements 36. A securing element 36 can include, for example, a notch, hook, latch, pin, or any other element used to fasten or fix a dilating component. The base 1 can include, for example, integral securing elements or a means for fixation of independent securing elements. In the embodiment of FIG. 25, the device comprises a base 1, an over-the-bridge component 2, and a plurality of elastic bands 8a; the base 1 further comprising a plurality of securing elements 36 to which one or a plurality (e.g. two) of elastic bands 8a fasten or secure. The securing elements 36 of this embodiment comprise notches located on the base 1 on either side of the nose. This arrangement provides for dilation on either side of the nose without dilation forces running over the bridge of the nose.

Figure 32:
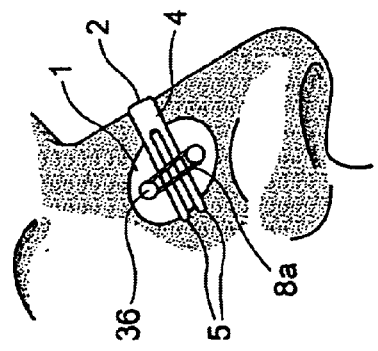

FIG. 32 discloses a base 1, an over-the-bridge component 2, a plurality of securing elements 36, and a plurality of elastic bands 8a. The over-the-bridge component 2 includes a resilient member 4 having ends 5. In this arrangement, the elastic bands 8a couple to securing elements 36 and tend to lift the upper and lower portions of the base 1. The lifting forces provide dilation of the nasal passage on either side of the nose without dilation forces from across the bridge of the nose. The resiliency of the ends 5 in this embodiment creates an axis from which the elastic bands 8a lift.

Figure 26:
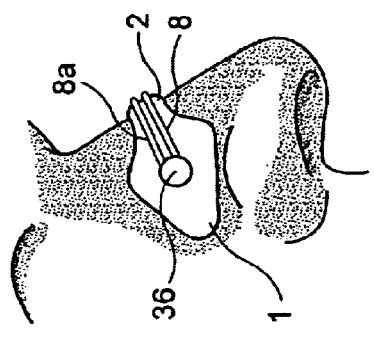

In another embodiment, as shown in FIG. 26, an arrangement may comprise a base 1, an over-the-bridge component 2, and an elastic member 8 such as an elastic band 8a, connected to a securing element 36 on each side of the nose. The dilation forces in this arrangement run across the bridge of the nose. As the elastic band 8a tends to return to its original position, the elastic band 8a presses against an over-the-bridge component 2. The force against the over-the-bridge component 2 causes the over-the-bridge component 2 to straighten thereby providing lifting dilation.

Figure 31:
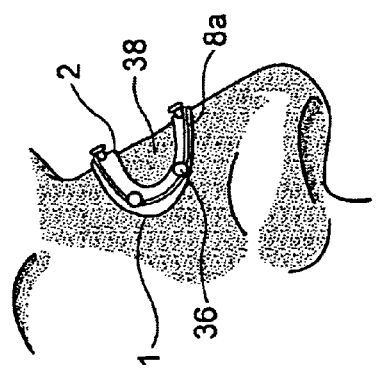
Figure 34:
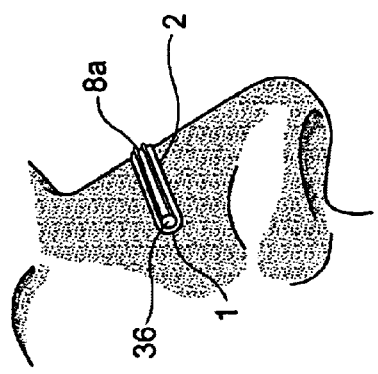
Figure 33:
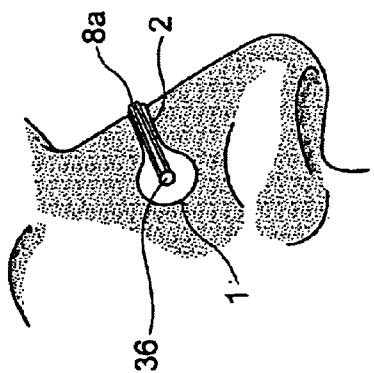

FIGS. 33 and 34 disclose arrangements similar to FIG. 26 having lower profiles to provide some users with more comfort. Of course, the use or application of multiple devices according to the present embodiments may be utilized. Another embodiment, as shown in FIG. 31, comprises a base 1 having an over-the-nose component 2, an elastic band 8a, and a plurality of securing elements 31. This arrangement also includes a void 38 configured at or near the center of the dilator device. The void 38 separates dilating forces to also provide some users with greater comfort.

A multi-component device can additionally provide selective incremental adjustment. The illustration in FIG. 27 discloses one embodiment having a base 1, an over-the-bridge component 2, a securing element 36, an elastic band 8a, and a plurality of incrementally spaced adjusters 10. The adjusters 10 may include, for example, hooks, notches, protrusion, grooves, etc. The adjuster 10 can be integral with the base 1 or over-the-bridge component 2 or be a separate component that fixes to the base 1 or over-the-bridge component 2.

Figure 28:
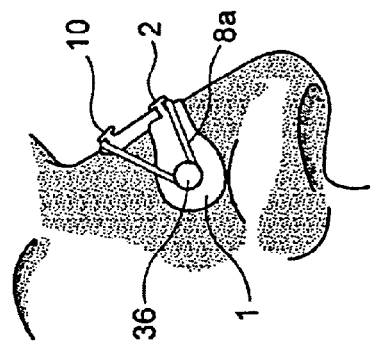
Figure 27:
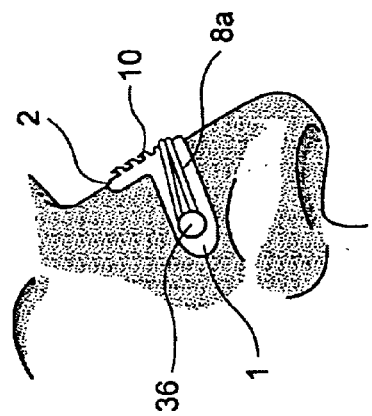

To illustrate, as the elastic band 8a is selectively positioned on the adjusters 10, the dilating force correspondingly adjusts. For example, placing the elastic member 8a higher on the adjusters 10 of the over-the-bridge component 2 shown in FIG. 27 creates a stronger dilating force. The illustrated position shown in FIG. 31 provides for the least dilating force. FIG. 28 discloses another adjuster arrangement. This embodiment provides for a triangular arrangement of elastic bands 8a lessening the potential of pinching and increasing some user's comfort.

Figure 36:
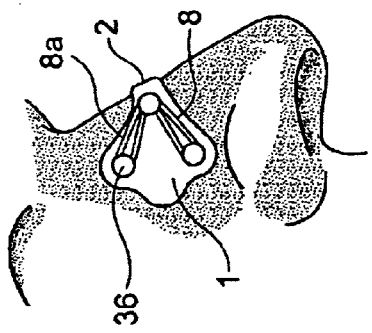
Figure 37:
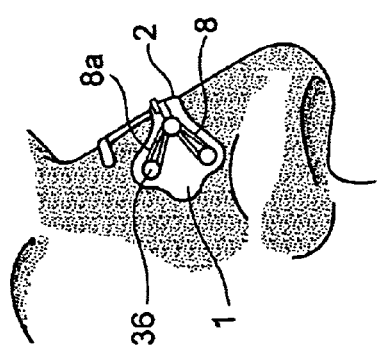

FIGS. 36 and 37 are all examples of multi-component dilator embodiments having various features as described earlier. The arrangements illustrated in FIGS. 36 and 37 provide for dilation lift to a larger area of skin on either side of the nose.

Figure 35:
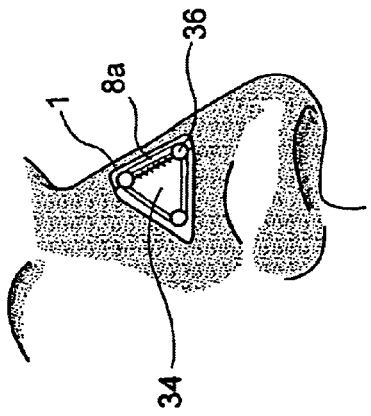

Referring to FIG. 35, the illustrated device combines the features of a lifting dilator, a multi-component dilator, and a bi-axial dilator. The device comprises a base 1, a flap 34, a plurality of securing elements 31, and an elastic band 8a. The base 1 and flap 34 can, for example, hinge at an axis that runs parallel to the bridge of the nose as shown by hash marks. The elastic band 8a and securing elements can be arranged in a triangle configuration. When this dilator arrangement is placed on the nose, the elastic band 8a pulls up or lifts the flap 34 along the axis, thereby creating dilation force.

Spline-Only Dilation

Figure 30:
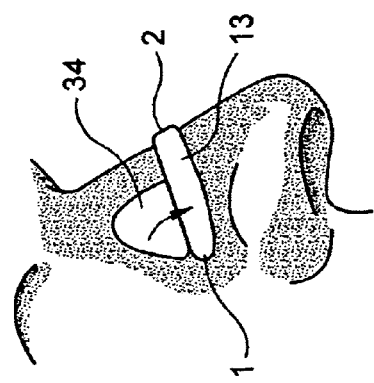
Figure 38:
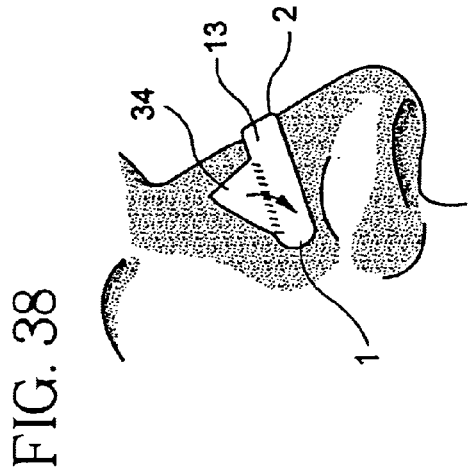

Another aspect of the present invention includes devices providing spline-only dilation. A spline-only dilator may comprises a base and an over-the-bridge component. The over-the-bridge component produces a dilating force when placed directly over the bridge of the nose. This type of design can reduce the cost of producing dilating devices. FIGS. 30 and 38 are other examples of spline-only dilators that also provide a multi-directional feature. The illustrations disclose a base I having a flap 34 and an over-the-bridge component 2. The over-the-bridge component 2 comprises a dilating spline member 13 that produces outwardly lifting dilation. The flap 34 provides a second lifting dilation in the direction shown by the arrow, for example, in FIG. 38.

Figure 29:
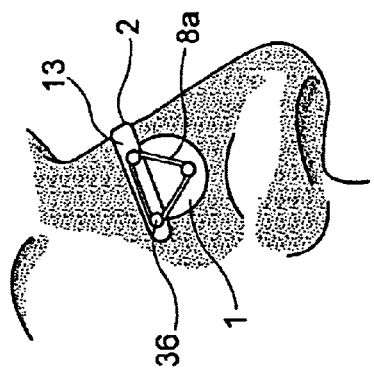

FIG. 29 shows a multi-component dilator having a base 1, an over-the-bridge component 2 comprising a spline dilating member 13, a plurality of securing elements 36, and a plurality of elastic bands 8a. This device is essentially the same as a spline-only dilator having multi-direction dilation with dilating properties created by elastic bands 8a as opposed to a flap.

Other Dilator Features

Referring to FIG. 4, some embodiments can include an over-the-bridge component 2 that comprises two layers of, for example, plastic to form an enclosed air pocket 14. The enclosed air pocket 14 provides a low level bulge along the center of the dilator that when deformed over the bridge of the nose, increases pressure within the pocket 14. Increased pressure within the pocket 14 increases lifting dilation. As with other devices disclosed herein, the over-the-bridge component 2 can be made of clear plastic.

Figure 20:
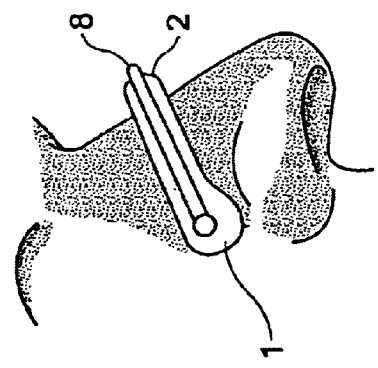

In some embodiments, such as that shown in FIG. 20, the device can comprise a base 1, an over-the-bridge component 2, and an elastic member 8 bonded to base 1. In this arrangement, the elastic member 8 produces dilation forces as the elastic member 8 contracts. The base 1 may or may not provide additional dilating forces.

Figure 21:
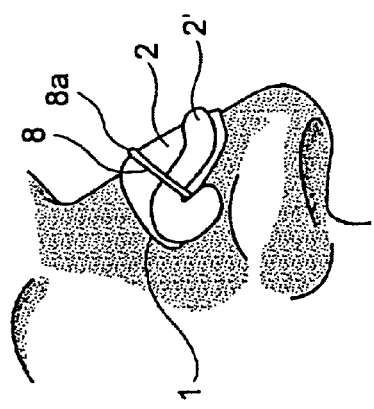

FIG. 21 illustrates an embodiment having a base 1, a first over-the-bridge component 2, a second over-the-bridge component 2', and an elastic member 8 such as an elastic band 8a. The second over-the-bridge component 2' can comprise a plastic non-dilating piece. The elastic band 8a of this arrangement is connected to the second over-the-bridge component 2' and provides dilation by contracting and lifting the second over-the-bridge component 2'.

Figure 24:
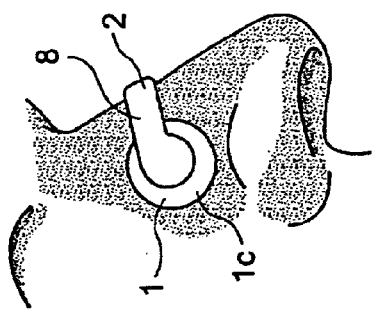

The device illustrated in FIG. 24 discloses a base 1 and an over-the-bridge component 2 comprising an elastic member 8. The base 1 can further comprise an adhesive pad 1c. The elastic member 8 contracts thereby providing dilating force. It should be appreciated that the dilating force is adjustable. In essence, the dilating properties of the device become stronger the further the base 1 is placed from the bridge of the nose. Some embodiments can include a portion of the over-the-bridge component which can be prepared from a resilient cushioning material, such as an open cell or closed cell foam. Dilation is produced when the foam contracts over the bridge of the nose causing the skin to lift over the nasal passages.

Figure 45:
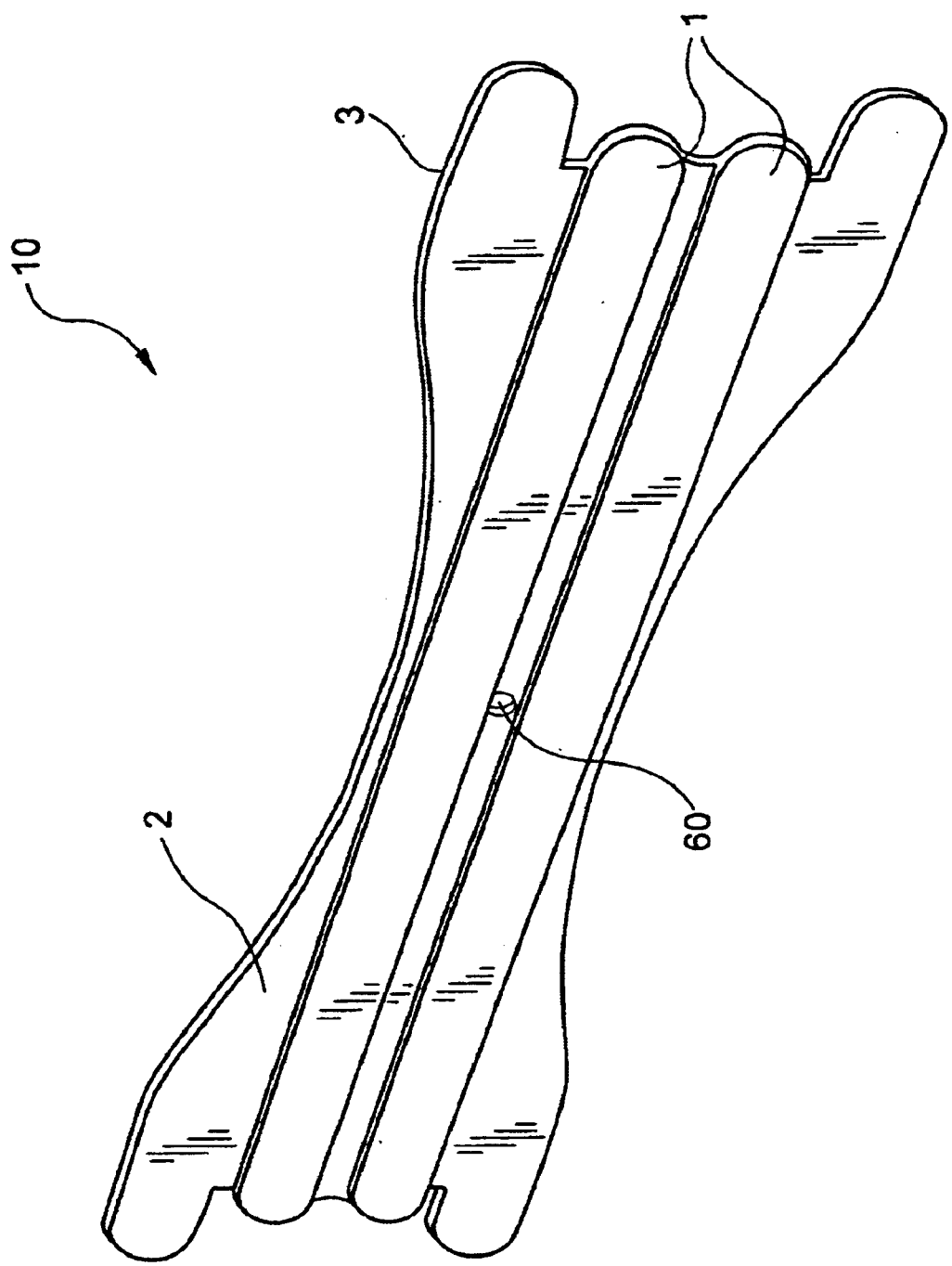

Other features of the herein disclosed devices will be appreciated from the drawings. For example, a device including a resilient member prepared from an open cell or closed cell material may be produced that optionally includes additional padding over at least one end of the resilient member to increase comfort and decrease the likelihood of painful contact proximate the nose of the user. Furthermore, the resilient member may include two or more resilient components configured to form a void therebetween which reduces the amount of the device which rests on a user's nose. In this embodiment, an example of which is depicted at FIG. 45, and in addition to other features, including one or more alignment mechanisms for assisting a user in properly applying the dilator device to the nose. In FIG. 45, this alignment feature is illustrated as an indicator 60 which comprises a port or aperture, although one or more such ports may be provided either in a straight line or as a design or other indicia to assist the user in applying the device.

Figure 39:
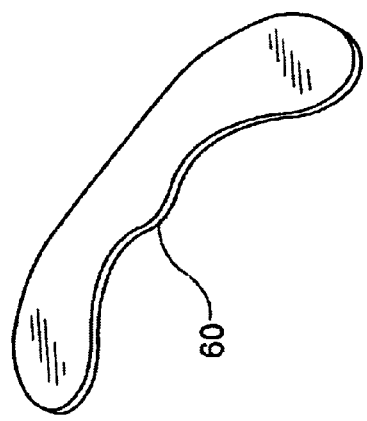

Referring to FIG. 39, such an alignment feature comprises a centering arch 61 to facilitate positioning of the dilator over a nose. The device further illustrates large tapered and rounded tabs at the ends to prevent accidental folding or curling of the ends during placement on the nose. FIG. 39 also illustrates a device with an indicator 60 in addition to other features and, as with most every embodiment set forth in this disclosure the device may be applied across (or over) the nose either in the orientation as depicted in the drawings, or inverted from the orientation depicted in the drawings. Other devices having a base may include wing features which when engaged to the local tissue region exert an upward force to the tissue to thereby dilate same.

Figure 40:
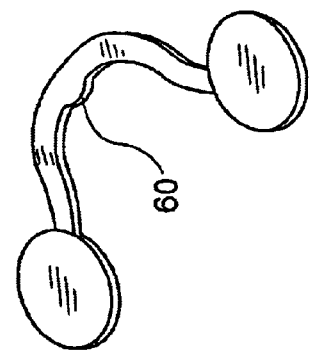

FIG. 40 illustrates an alternative configuration for an over-the-bridge component 2 and an indicator 60.

Figure 41:
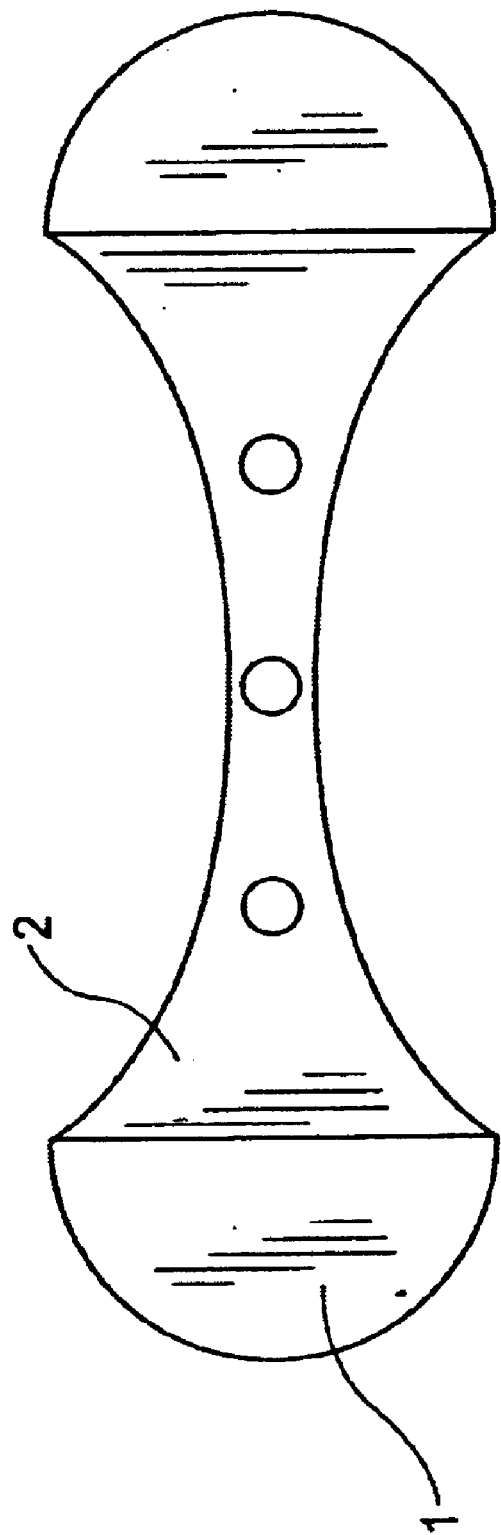

FIG. 41 illustrates a device including a portion of base 1 and an over-the-bridge component 2 which can be elastic. In other related embodiments, the base and over-the-bridge component can all be made from an elastic material or from a resilient material.

Figure 42A:
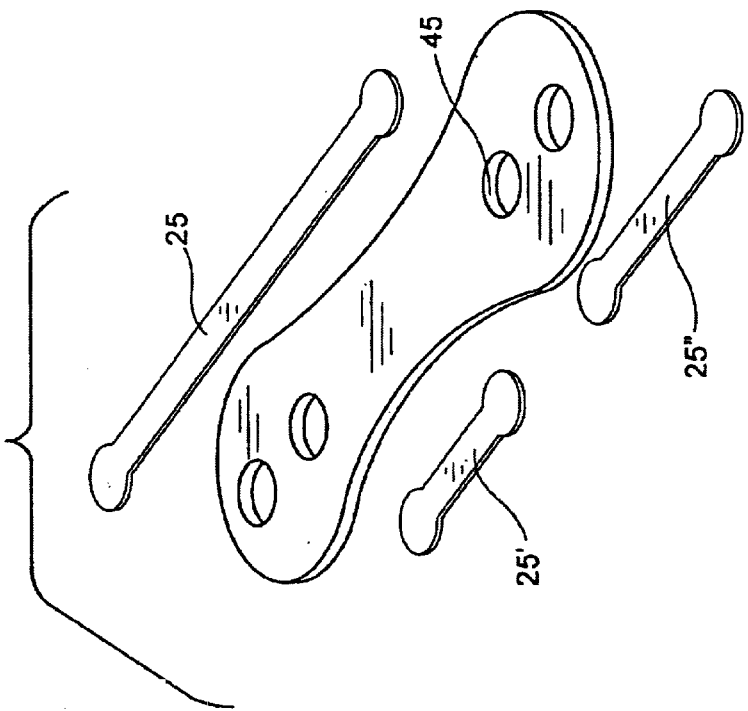
Figure 42:
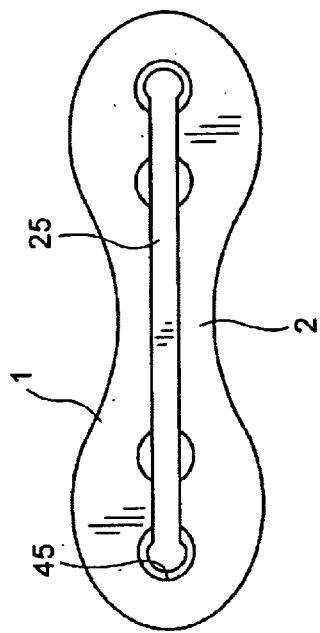

FIGS. 42a–b depict an embodiment including a base member 1, having an over-the-bridge portion 2 and having a series of apertures 45 disposed along a longitudinal axis of the base member 1 so that a resilient body member 25 may be releasably coupled to, and received by, the apertures 45. In this embodiment, the resilient body member 25 may be sized to fit in any two of said apertures 45 thereby providing an adjustable magnitude of lifting force to the base member 1. The ends of resilient body member 25 may be formed to provide a friction fit to the apertures 45 or may be provided with adhesive material to promote the mechanical coupling therebetween. In this embodiment several different attachment mechanisms and materials may be utilized to create the desired dilation. For example, many ports 45 may be provided in the body 1 of the dilator to receive one or more elongate members. As depicted in FIG. 42a, a first upper member 25 may have resilient properties (i.e., sustain a restoring force when bent or deformed from an original state) and may be directly coupled to any two ports 45 formed in the body 1 of the dilator. The member 25 may be one of a set of different members that each provide a different magnitude restoring force so that a user may select an appropriate magnitude of lifting force as desired by the user. In addition, one or more addition members 25',25" may be coupled to the body 1 or may be affixed or formed to receive the elongate first member 25 through the ports 45. The additional members 25',25" may be formed of a material different than the material of first member 25. The additional members may be formed of an elastic material and/or an adhesive material. As noted, these additional members may have a selected resilient (or elastic) force due to their chosen material composition, their length and the location at which they couple to the body 1. The additional members 25',25" may have portions formed to receive and retain the ends of the first member 25, such a socket to receive a corresponding ball portion of the first member 25, and the like.

Other embodiments of a tissue dilator may have a dual set or more resilient body members 25 with fastened with, for example, micro hook and loop type material on opposing sides of the body members so that they mechanically couple together and thus provide additional lifting force when combined. The base member of such a device also may be covered with a complementary layer of such micro hook and loop material to retain the first resilient body member to the exterior of the base member. A related embodiment having a single resilient member coupled to an elastic member of similar dimension may also be provided according to this embodiment. An adhesive layer of material is preferably provided on the base member on the side opposite to the resilient body members to promote adhesion to a local tissue area and an additional layer of adhesive. In these and other alternative embodiments of the present invention, the adhesive layer or portion that typically (and preferably) adheres the dilator to the local tissue region may be configured to be re-usable. In these embodiments, a pad member may slideably engage one or more resilient members so that during use the combination is retained in place. When the dilator device is removed by a user, the pad members may be manually removed and another substituted when the user is ready to apply another dilator device. The pad member may be adhered with a releasable adhesive, may be connected with a friction fit coupling, may be attached with a screw or threaded shank and the like. The net benefit to the user relates in part to the fact that once the user locates a resilient member having a magnitude of restoring force desired by the user, that same resilient member may be used on at least several different occasions with the same results. These embodiments allow for fabrication and use of a relatively expensive, customized resilient member fabricated for a single user or a group of users who desire a certain magnitude of force or a certain size of resilient member (and in most embodiments dilator device) that best promotes respiration for said user.

Other related embodiments relate to those just described, may have each end of a single resilient body member disposed in a set of pockets formed at each end of the base member. These pockets may be adhered, or heat sealed, laminated, connected with hook and loop fasteners and the like. This embodiment allows a user to install a variety of different resilient body members to provide differing levels of lifting force and/or having different physical dimensions to promote dilation of a local tissue region. Each one of said pockets may be retained with an adhesive or one side adhered and another fastened with micro hook and loop type fastener material and an adhesive layer 3 provides a means to couple the device to a local tissue region on at least each end of the body 1.

Yet another embodiment related to those just discussed, wherein a resilient body member is disposed in a cavity formed by an top layer of material which is preferably heat laminated or adhered to mechanically coupled to retain the resilient body member within said cavity. A layer of adhesive material is disposed on the reverse side of the base member to provide adhesion to a local tissue region. The cavity may be size to allow the resilient body member to move slightly within said cavity so that no undue binding or wear occurs during use and/or during storage or shipment of the dilator devices to an end user.

Another related embodiment of the present invention as described immediately above, in which an additional elastic layer is provided intermediate the adhesive layer and the base member and wherein a pocket or cavity is formed to retain the resilient body member in place during use. As noted, heat lamination, micro hook and loop type fastener material(s), or pressure sensitive adhesive may be used to fabricate the devices in this series of related embodiments of the present invention. The additional elastic layer, provides added resiliency to the structure and, as depicted, the base member may be severed so that just an end portion is coupled to the elastic layer and the resilient body member.

Figure 43:
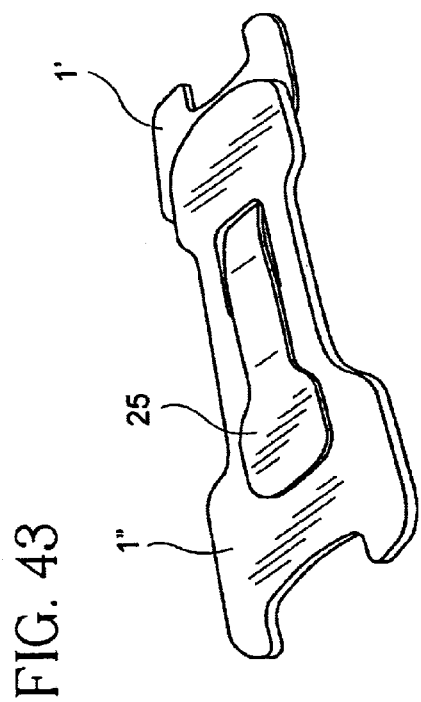
Figure 43A:
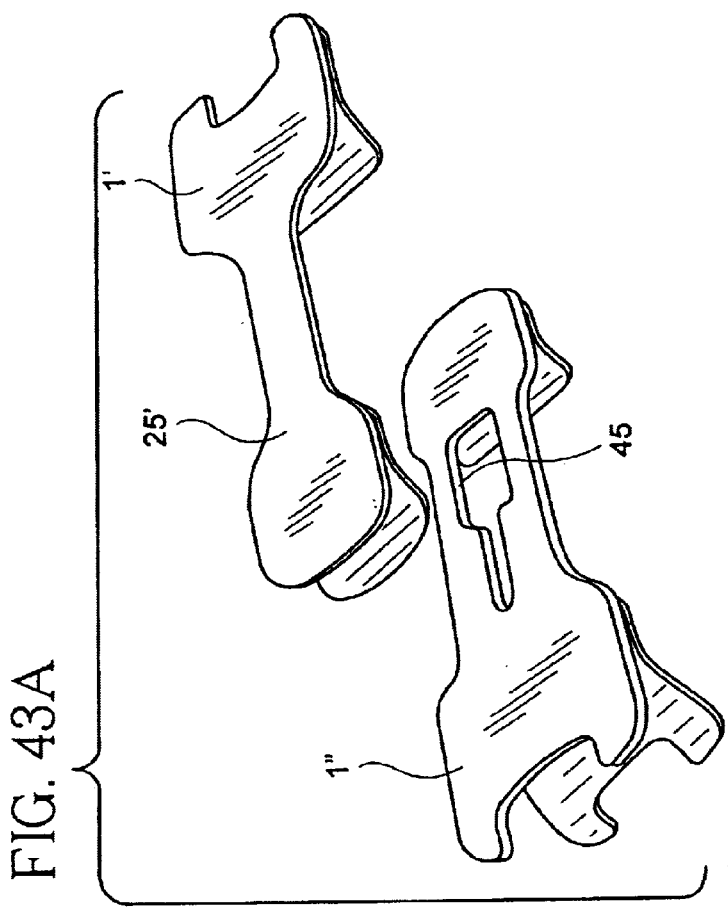

FIGS. 43a–b depicts an embodiment of the present invention wherein the base member 1 is two interlocking base member portions 1',1" and have an integral resilient body member portion 25 formed as a part of one of said two interlocking base member portions 1',1". An aperture 45 formed in one of said interlocking members 1" receives the resilient body member portion 25 and the body member portion 25 is adhered to the other interlocking member 1'. This inherently adjustable device may thus be manipulated and adjusted by a user to provide a varying amount of lifting force to a local tissue region and/or to provide a different size (i.e., length) to the assembly. In this embodiment, the length and/or the magnitude of the force promoting dilation may be adjusted by the user after adhering each end of the device to respective local tissue regions proximate the nasal passages to be dilated. That is, the interlocking members 1', 1" are not adhered to each other (i.e., a release liner is retained in place) and the user pulls said members 1', 1" together and then adheres them to each other when they sense a desired magnitude of force applied to the local tissue region.

Figure 44:
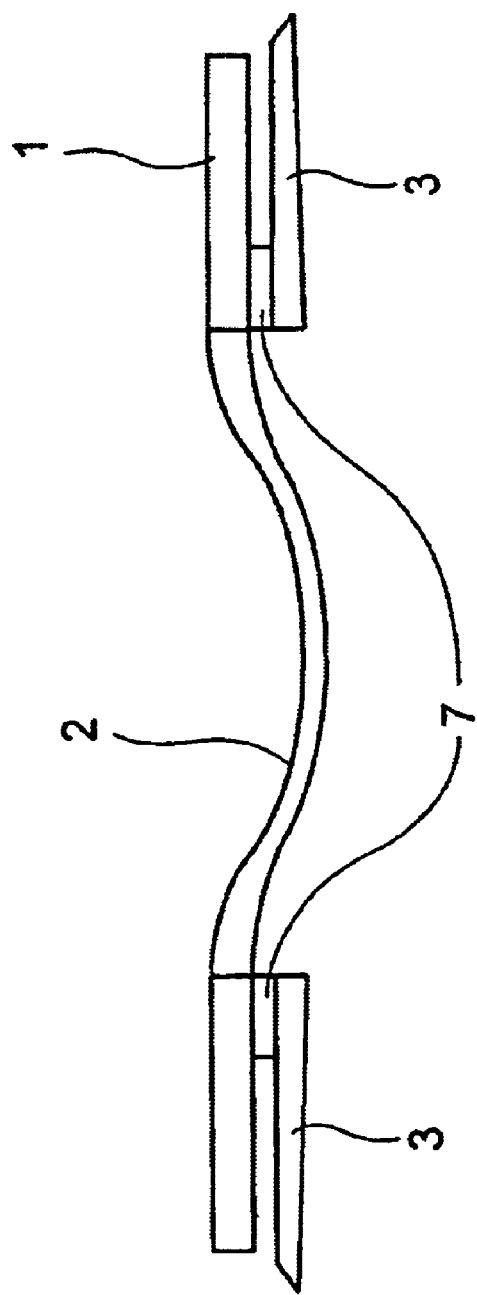

FIG. 44 depicts an embodiment of the present invention wherein the over-the-bridge portion 2 of the base member 1 is pre-formed into a desired single curve shape and the ends of the base member 1 are substantially straight. A pair of bonding pads 3 provided with an adhesive material disposed on the exterior surface thereof are coupled to the ends of the base member 1 to retain the device in place proximate a local tissue region during use. In the embodiment depicted at FIG. 44, the pair of bonding pads 3 are connected to the base member 1 with a small extension member 7 affixed to the side of the pre-formed base member and when coupled to the local tissue region the pre-formed over-the-bridge portion 2 is bent back toward the single curve shape to thereby promote a lifting force substantially orthogonal to the surface of the local tissue region. In the embodiment depicted (in part) in FIG. 44b, in lieu of the bonding pad and the small extension member 7 the base member 1 has a formed portion or area 3' that provides for a stand-off boss area upon which adhesive material is applied, but otherwise performs a similar function to that set forth by the bonding pads 3 depicted in FIG. 44a. The extension member 7 may be formed of an elastic material such as closed cell form to absorb and distribute the lifting force of a resilient member coupled thereto and/or to promote the desired orthogonal lifting force to the local tissue region. Alternatively, the extension member 7 may be formed of a relatively rigid material additional to more fully transmit the lifting force of the resilient member. Of course, the small extension member 7 may be formed integrally to the entire dilator device so that said extension member 7 is a ridge, or boss 7, of material extending above, or spaced apart from, the general planar portion adjacent to said member 7. In this regard, the member 7 may be additional material or may be essentially the same thickness as the rest of the adjacent portion of the dilator device (i.e., hollow or without structure disposed underneath said member 7).

Referring now to FIG. 45, a dilator device 10 of the invention can include one or more resilient members 1, a surface layer 2 on a first side of the device and an adhesive layer 4 on at least a part of a second side of the device for securing the device to a local tissue region. A port 60 (or a plurality of ports 60—not shown) may be provided to facilitate alignment as earlier described herein. The resilient member(s) 1, surface layer 2 and adhesive layer 3 can be made from materials and assembled as disclosed in, for example, U.S. Pat. Nos. 5,533,499 and 5,549,103 the entire contents of which are hereby incorporated by reference herein.

Referring to FIG. 45, a complex shape resilient member 1 having major portions spaced apart and coupled with short segments, or continuous portions 4, coupling the spaced apart major portions helps provide a distributed lifting force to the local tissue area. A related embodiment to that depicted in FIG. 45 having such continuous portions 4 only coupling the major portions of the resilient member intermediate (and not at or proximate the ends thereof) provides even more evenly distributed lifting force (and allows the ends portions to individually lift the proximate local tissue region thereof. Of course, more than two major portions may be created and each may or may not be coupled to each of the other of said major portions. It will be appreciated that that embodiment of the device 10 of FIG. includes a plurality of continuous portions 4 between resilient members 1 although a single such portion 4 may be provided coupling adjacent major portions.

Figure 46:
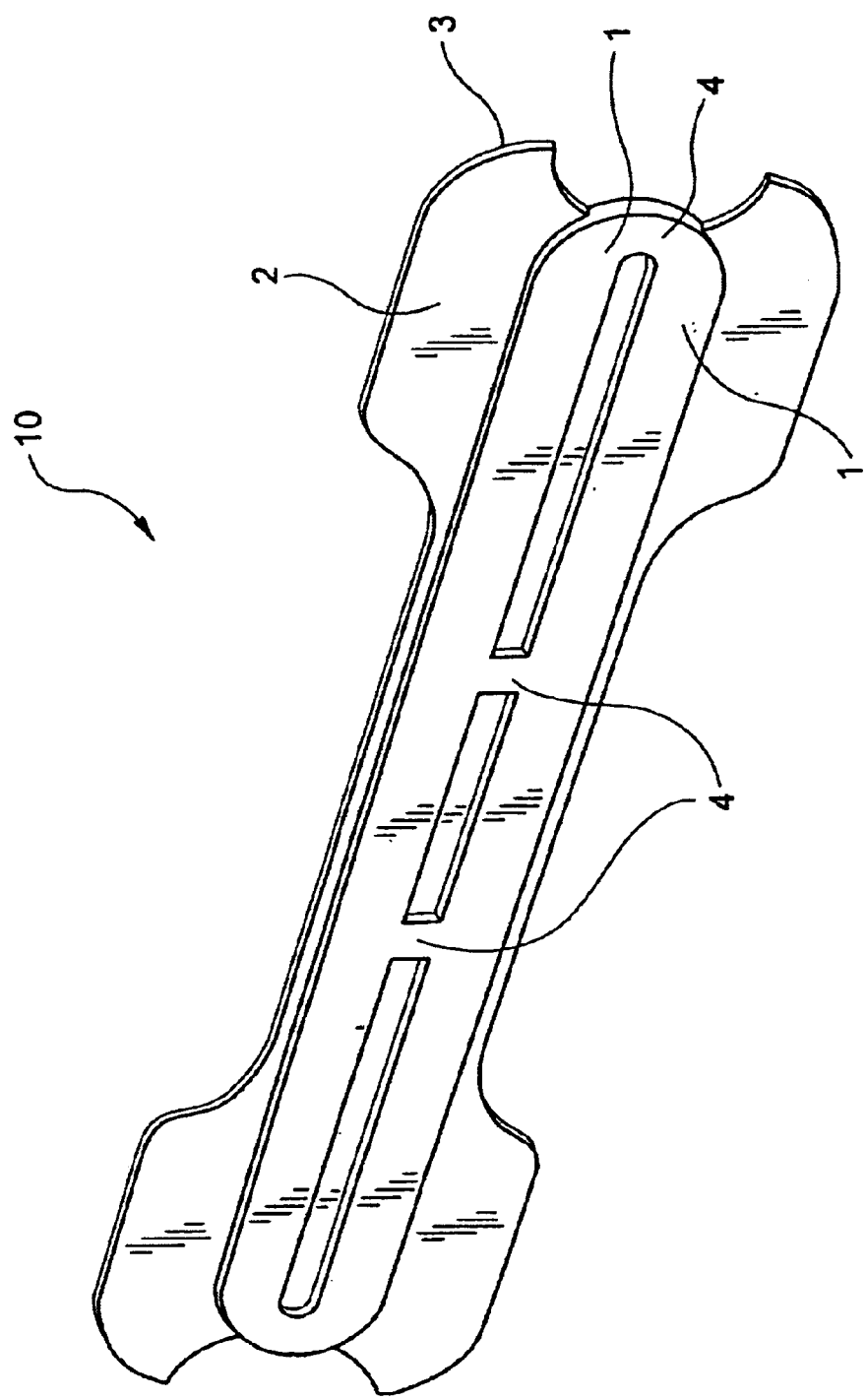
Figure 47:
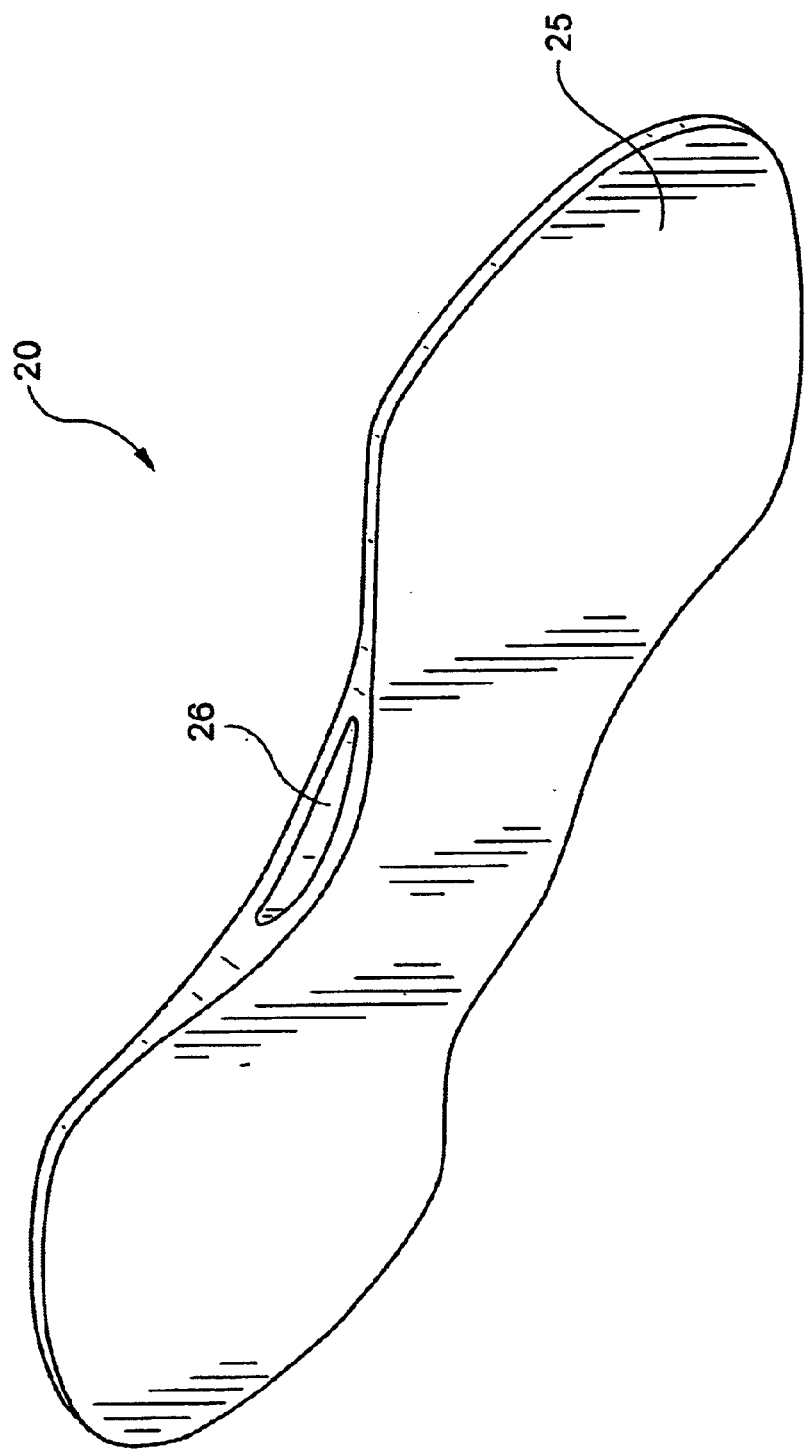

Referring to FIG. 46, an alternative embodiment of a device 20 according to the present invention is illustrated fabricated using extrusion methods of manufacture. In this embodiment, a resilient body 25 of device 20 can be punched from an extruded plastic bar using known methods including those disclosed, for example, in U.S. Pat. No. 6,029,658. The extrusion can be either the long axis or the short axis of a device 20. An adhesive can then be applied to form adhesive layer 26 or an adhesive material may be co-extruded at the same time the extruded plastic (or other material) bar is produced. Alternatively, the bar of extruded material may itself be formed of a suitable adhesive material so that the entire device 20 including the body 25 of the device 20 are rendered adhesive. It will be appreciated that a surface layer (not shown) can also be applied to the device 20, which is particularly desirable in the event that the device 20 itself is entirely rendered of adhesive material.

In another embodiment illustrated in FIG. 4, a device 30 can include at least two different components which are co-extruded or extruded separately and then combined into an integral article using known methods. As illustrated, a first component 35 can be co-extruded with a second component 36 or the first component 35 and the second component 36 can be separately extruded and subsequently combined. Additional components can also be extruded (co-extruded or "tri-extruded" and the like). A layer of adhesive material may be applied to one side and a protective surface layer (not shown) may be disposed on a second side of device 30, or, as noted above, an adhesive material may be combined with the original extrusion material to render at least one side of the device 30 adhesive.

Thus, for example, in this embodiment, device 30 can include a resilient polyurethane component 36 and an open cell or closed cell plastic component 35 (such as an open cell or closed cell polyurethane) to facilitate use comfort at a location where a device 30 extends over the bride of a nose (or other local tissue region) to be dilated. The material chosen for this embodiment may itself be adhesive in nature (and may be optionally covered entirely or on a side thereof with a release layer).

Figure 48:
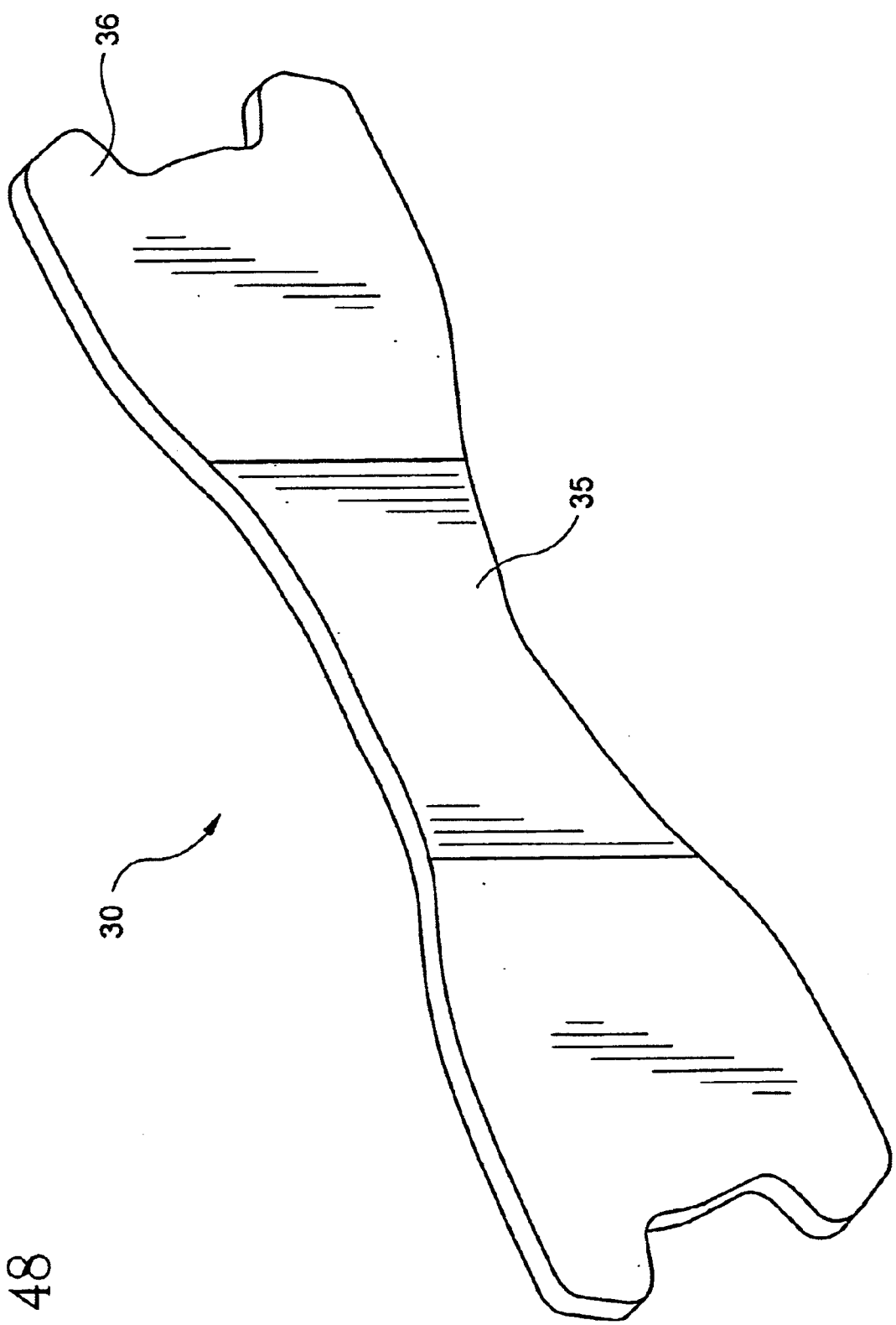

Alternatively, referring to FIG. 48, component 36 can provide for a first amount of resiliency and component 35 a second amount of resiliency, the resiliency of components 35 and 36 can be the same or different in magnitude. Illustrated by reference to FIG. 48 is another alternative embodiment of a first component 35 and a second component 36 having a substantially planar centrally-located resilient region which is best fabricated using the "short axis" extrusion methods elsewhere described herein. In this embodiment, a closed bubble or cavity open to ambient pressure may be formed in the middle or near the ends of the member 30 to promote comfort and assist in directing the lifting force to the preferred orthogonal orientation relative to the local tissue region.

The materials forming extruded component 35 can be the same or, typically, different than that of extruded component 36. Examples of materials suitable for extruded components 35 and 36 include, without limitation, thermoplastic resins such as poly (acrylonitrile-co-butadience-co-styrene) polymers, acrylic polymers such as polymethylmethacrylate, poly-n-butyl acrylate, poly (ethylene-co-acrylic acid), poly (ethylene-co-methacrylate), etc.; fluoropolymers including polytetrafluoroethylene (i.e., teflon®), poly (ethylene-co-tetrafluorethylene) co polymers, (tetrafluoroethylene-co-propylene) copolymers, polyvinyl fluoride polymers, etc., polyamides such as nylon 6, nylon 6,6 etc.; polycarbonates; polyesters such as poly(butylene-co-terephthalate); poly(ethylene-co-1,4-naphthalene dicarboxylate), poly(butylene-co-terephthalate), polyimide materials; polyethylene materials including low density polyethylene; linear low density polyethylene, high density polyethylene, high molecular weight high density polyethylene, etc.; polypropylene, biaxially oriented polypropylene; polystyrene, biaxially oriented polystyrene; vinyl films including polyvinyl chloride, (vinyl chloride-co-vinyl acetate) copolymers, polyvinylidence chloride, polyvinyl alcohol, (vinyl chloride-co-vinylidene dichloride) copolymers, specialty films including polysulfone, polyphenylene sulfide, polyphenylene oxide, liquid crystal polyesters, polyether ketones, polyvinylbutyrl, and the like.

Referring now to yet other embodiments of the present invention, a dilator device may include one or more resilient members, a surface layer, an adhesive layer and an alignment guide such as an orifice or aperture, reflective indicia, a design, a series of apertures, a linear indiciate, a ridge, a boss and the like that is readily detected by the user of the dilator and assists such user in accurately aligning and applying said dilator. In this embodiment, the alignment guide may be centrally located in a transverse dimension along a longitudinal axis of the device and can thus facilitate positioning of the device when applying the device over the bridge of a nose, or other local tissue region to be dilated. It will be appreciated that the alignment guide (or guides) need not be positioned on the longitudinal axis and may be configured of a wide variety of features to assist the user in applying the device accurately to the local tissue region. Device may include one or more apertures (not shown) in alignment, or may comprise a ridge, reflective indicia, geometric indicia, design indicia, an apex feature, a boss, or a region of increased thickness, as mentioned above.

In yet another embodiment of dilator devices of the present invention, it will be appreciated that the alignment guide can also be positioned along a continuous portion extending between one or more resilient members1 disposed on said dilator.

From the foregoing detailed description and examples, it will be evident that modifications and variations can be made in the products and processes of the invention without departing from the spirit or scope of the invention. Therefore, it is intended that all modifications and variations not departing from the spirit of the invention come within the scope of the claims and their equivalents.

We claim:

1. A method of use for a tissue dilator, comprising the steps of:
   providing a tissue dilator having a top surface, an adhesive surface, and a resilient member, said dilator having an alignment feature which is generally centrally located between a pair of ends, said alignment feature being a generally linear ridge defined on the top surface as an area of increased height relative to other portions of the top surface, said ridge being aligned in a generally transverse direction relative to a longitudinal axis of the tissue dilator;
   aligning an alignment feature of a tissue dilator with the nasal ridge portion of a subject;
   compressing the tissue dilator on each side of said alignment feature to a local tissue region.

2. A method according to claim 1, wherein the step of aligning includes the step of visually referencing the ridge alignment feature.

3. A method according to claim 1, wherein the step of aligning includes the step of tactilely referencing a centrally located alignment feature.

4. A method according to claim 1, wherein the step of compressing the tissue dilator results in generally symmetric application of the tissue dilator relative to the nasal ridge.

5. A method of use for a tissue dilator, comprising the steps of:
   providing a tissue dilator having a top surface, an adhesive surface, and a resilient member, said dilator having a linear alignment feature which is generally centrally located between a pair of end, said alignment feature being an area of increased thickness relative to the other portions of the tissue dilator, said alignment feature being aligned in a generally transverse direction relative to a longitudinal axis of the tissue dilator;
   aligning the alignment feature with the nasal ridge portion of a subject; and compressing the tissue dilator to adhesively secure the tissue dilator onto the subject.

6. The method of claim 5 wherein the alignment feature is a linear ridge feature which is aligned with the nasal ridge of the subject upon application.

7. The method of claim 5 wherein the step of aligning includes the step of visually referencing the alignment feature and visually directing the alignment feature to the nasal ridge portion of the subject.

8. The method of claim 5 wherein the step of aligning includes the step of tactilely referencing the alignment feature and tactilely directing the alignment feature to the nasal ridge portion of the subject.

9. The method of claim 5 wherein the step of providing a tissue dilator includes the step of providing a multi-part resilient member.

10. A method of use for a tissue dilator, comprising the steps of:

providing a tissue dilator having a top surface, an adhesive surface, and a resilient member, said dilator having an alignment feature on the top surface which is generally centrally located between a pair of ends, said alignment feature being a generally linear area of increased thickness relative to the other portions of the tissue dilator, said aligiment feature being aligned in a generally transverse direction relative to a longitudinal axis of the tissue dilator;

grasping the tissue dilator;

identifying the alignment feature;

directing the tissue dilator into a generally symmetric orientation relative to a nasal ridge of a subject; and adhesively securing the tissue dilator to the subject.

11. The method of claim 10 wherein the alignment feature is a linear ridge feature which is aligned with the nasal ridge of the subject upon application.

12. The method of claim 10 wherein the step of directing includes the step of visually referencing the alignment feature and visually directing the alignment feature to the nasal ridge portion of the subject.

13. The method of claim 10 wherein the step of directing includes the step of tactilely referencing the alignment feature and tactilely directing the alignment feature to the nasal ridge portion of the subject.

\* \* \* \* \*